United States Patent
Bernstein

(10) Patent No.: US 8,328,722 B2
(45) Date of Patent: Dec. 11, 2012

(54) METHOD FOR AESTHETICALLY TREATING CELLULITE SKIN BY LIPOTOMY, AND DEVICE FOR IMPLEMENTING SAID METHOD

(75) Inventor: Serge Bernstein, Epinay sur Seine (FR)

(73) Assignee: Serge Bernstein, Epinay-sur-Seine (FR)

( * ) Notice: Subject to any disclaimer, the term of this patent is extended or adjusted under 35 U.S.C. 154(b) by 78 days.

(21) Appl. No.: 12/995,329

(22) PCT Filed: May 30, 2008

(86) PCT No.: PCT/FR2008/000736
§ 371 (c)(1),
(2), (4) Date: Mar. 23, 2011

(87) PCT Pub. No.: WO2009/144389
PCT Pub. Date: Dec. 3, 2009

(65) Prior Publication Data
US 2011/0166452 A1    Jul. 7, 2011

(51) Int. Cl.
*A61B 8/00* (2006.01)
(52) U.S. Cl. .................. 600/438; 600/407; 600/437
(58) Field of Classification Search .......... 600/407–410, 600/437–469
See application file for complete search history.

(56) References Cited

U.S. PATENT DOCUMENTS

| | | | | |
|---|---|---|---|---|
| 4,183,249 | A | * | 1/1980 | Anderson .................. 73/626 |
| 4,817,614 | A | * | 4/1989 | Hassler et al. .............. 600/441 |
| 5,031,627 | A | * | 7/1991 | Yost et al. .................. 600/442 |
| 5,208,747 | A | * | 5/1993 | Wilson et al. .............. 600/443 |
| 5,419,761 | A | * | 5/1995 | Narayanan et al. .......... 604/22 |
| 5,520,183 | A | * | 5/1996 | Lake et al. ................. 600/453 |
| 5,941,825 | A | * | 8/1999 | Lang et al. ................ 600/449 |
| 6,013,031 | A | * | 1/2000 | Mendlein et al. ........... 600/442 |
| 6,030,374 | A | | 2/2000 | McDaniel |
| 6,318,146 | B1 | * | 11/2001 | Madsen et al. ............. 73/1.86 |
| 6,358,208 | B1 | * | 3/2002 | Lang et al. ................ 600/438 |
| 6,524,250 | B1 | * | 2/2003 | Weber et al. .............. 600/439 |
| 6,635,486 | B2 | * | 10/2003 | Madsen et al. .............. 436/8 |
| 6,659,949 | B1 | * | 12/2003 | Lang et al. ................ 600/438 |
| 7,860,547 | B2 | * | 12/2010 | Kondoh et al. ............. 600/407 |
| 2005/0096682 | A1 | | 5/2005 | Daffer |
| 2006/0206040 | A1 | | 9/2006 | Greenberg |

FOREIGN PATENT DOCUMENTS

| | | |
|---|---|---|
| DE | 199 04 907 A1 | 9/2000 |
| EP | 1 655 057 A1 | 5/2006 |
| WO | WO 99/34857 A | 7/1999 |

OTHER PUBLICATIONS

Dr. Jean-Marc Benchimol "La Lipotomile" *Internet (online)*, Feb. 22, 2006 XP-002519195.

* cited by examiner

*Primary Examiner* — Sanjay Cattungal
(74) *Attorney, Agent, or Firm* — Womble Carlyle Sandridge & Rice, LLP

(57) ABSTRACT

The invention relates to a method for aesthetically treating cellulite skin by lipotomy, and to a device for implementing said method.

13 Claims, 2 Drawing Sheets

Figure 1:
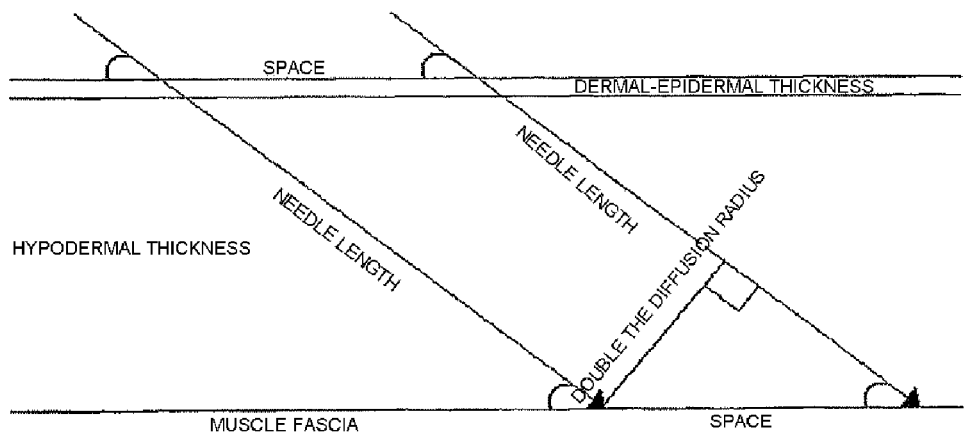

METHOD FOR AESTHETICALLY TREATING CELLULITE SKIN BY LIPOTOMY, AND DEVICE FOR IMPLEMENTING SAID METHOD

The invention relates to a method for esthetically treating cellulite skin by lipotomy, and also to a device for implementing this method.

The invention is part of the field of superficial esthetic skin treatments.

The terms "cellulite skin" or "cellulite", used for the purpose of the present invention, refer exclusively to an esthetic cellulite which causes dents known as "orange peel" on the skin. This unsightly "padded" appearance of the skin is due to a very localized hypertrophy of subcutaneous adipose tissue resulting from fat storage.

Under the skin, which is composed of the epidermis and the dermis, there is an adipose tissue. The metabolism of this layer of fat is mainly under hormonal control. This layer is thick in women, and is responsible for the appearance of cellulite, generally after puberty. This is because cellulite is a secondary sexual characteristic specific to the female sex. Although normal, it is unsightly.

Subcutaneous adipose tissue is composed of cells, in particular adipocytes.

Some techniques, such as lipotomy, are already known for treating unsightly lumps of cellulite fats. Lipotomy is a method for esthetically treating cellulite skin, the aim of which is to make the adipocyte membrane fragile and to obtain, in the end, lysis of this membrane and destruction of the adipocytes. The cell membranes are made fragile through the entry of solvent into the adipocytes following the induction of a difference in osmotic pressure on either side of said membranes.

As is well known to those skilled in the art, the osmole (Osm) is a physical unit of measurement of osmotic pressure, expressed in moles per liter. When one mole of an osmotically active substance is dissolved in one liter of water, it has an osmotic value of one osmole. The osmotic pressure corresponds to the difference in the osmotic values on either side of the semipermeable membrane owing to two liquids which do not have the same richness in dissolved osmotically active molecules. The osmolarity corresponds to the concentration relative to the molecular weight of dissolved substances exerting an osmotic capacity, and is also expressed in osmoles. It can be considered that the osmolarity with respect to diffusible electrolytes of the intracellular and extracellular sector is approximately 300 mOsm.

A difference in osmotic pressure—due to an osmolarity gradient—between two sectors separated by a semipermeable membrane is reflected by a flow of solvent directed to the sector with the highest osmolarity.

The cell membrane can be likened to a semipermeable membrane.

Thus, in order to induce a flow of liquid into adipocytes and thus to obtain an intracellular hyperhydration, a hypotonic solution, i.e. a solution of which the osmolarity is much lower than that of the intracellular medium, is administered into the fatty tissue. Such an administration, which makes it possible to infiltrate the tissues, is commonly carried out by injection. Following this injection, a flow of solvent, in the case in point water, penetrates into the adipocytes, creating a rapid increase in intracellular volume and a thinning of the cytoplasmic membrane, resulting in this cell membrane becoming fragile, possibly to the extent that it ruptures.

More specifically, it is a question of inducing cell destruction controlling the hypo-osmolarity caused by the treatment by virtue of safety and efficacy parameters. This treatment is applicable to all types of tissue: fatty tissue, cellulite tissue and tumor tissue. In the case of cellulite tissue or fatty tissue, the treatment is combined with ultrasound and, secondarily with vibration, then having the name lipotomy.

Lipotomy is a technique which, at the beginning, could give rise to serious accidents such as tissue and skin necrosis. These accidents generally resulted from an overdose during the administration of the hypotonic solutes used.

While it is today more successfully controlled, the results obtained can nevertheless sometimes show a lack of reproducibility depending on patients and on the areas treated.

Osmosis phenomena begin to cause cell membrane rupture starting from a threshold value which is commonly referred to as "hypo-osmolarity threshold". Moreover, the membrane rupture becomes complete below a value which is commonly referred to as "limiting value". The cell membrane of red blood cells serves as a model for all other cells. Tests assessing the threshold value and the limiting value are part of the general nomenclature of laboratory tests assessing the resistance of red blood cells to hypo-osmolarity in order to search for abnormal fragility. The hypo-osmolarity or hypotonicity of these media in vitro is realized by means of a dilution of sodium chloride. In this model, the osmolar media consist of injectable water as solvent and of sodium chloride as solute. The physiological medium is represented by a solute of 9 grams per liter of solvent. The threshold value is reached starting from 5 grams per liter of sodium chloride and the limiting value starting from 3 grams per liter of sodium chloride.

Methods for treating fatty tissues can be classified into three groups by virtue of the following model:
i) Group 1: Ineffective treatments, i.e. carried out at an osmolarity above the threshold value,
ii) Group 2: Partially effective treatments, i.e. carried out at an osmolarity between the threshold value and the limiting value, and, finally
iii) Group 3: Totally effective treatments, i.e. carried out at an osmolarity below the limiting value.

Depending on the type of treatment desired, the aim is to reproduce, in vivo, the conditions of partial or total effectiveness. Treatments for fatty or cellulite tissue will seek a partial effectiveness, whereas the treatment of cancerous tumors will have to be totally effective.

The mode of action acts by osmolar difference between the cell and its medium. This difference is referred to as the "osmolar gradient".

The osmolar gradient (O.G.), expressed in grams of solute per liter, corresponds to the following equation:

$$O.G. = \text{Osmolarity of the physiological medium (g/l)} - \text{Threshold value (g/l)}$$

Thus, given that the osmolarity of the physiological medium is 9 g/l, the osmolar gradient of the threshold value is equal to 9−5, i.e. 4 g/l. Likewise, the osmolar gradient of the limiting value is equal to 9−3, i.e. 6 g/l.

The partial effectiveness is obtained for an osmolar gradient ranging from 4 to 6 grams per liter of sodium chloride solute. The total effectiveness is obtained starting from an osmolar gradient of greater than or equal to 6 grams per liter of sodium chloride solute.

The problem addressed consists in transposing in vivo in humans the data known in vitro.

However, it is not at all easy to precisely determine the volume of hypotonic solution to be injected and/or its osmolarity according to the area of fatty tissue to be treated, which produces the drawbacks set out above.

The present invention therefore aims to improve the method for esthetically treating cellulite skin that is lipotomy, in particular in terms of safety and reproducibility, while at the same time obtaining optimum effectiveness.

To this effect, the invention relates to a method for esthetically treating cellulite skin of a patient by lipotomy, characterized in that it comprises at least the following steps:

1) determination of the skin surface of an area to be treated by means in particular of a grid on the skin,
2) ultrasonographic evaluation of the volume of fatty tissue underlying said surface of the area to be treated, at rest,
3) ultrasonographic evaluation of the volume of fatty tissue underlying said surface of the area to be treated, said tissue being compressed to the maximum,
4) calculation of the percentage (BI or Bernstein Index) represented by the volume of the extracellular sector of said tissue within said area, considering the volume represented by the cells of the fatty tissue to be incompressible, according to the following equation (1):

$$BI (\%) = E_0 - E_P / E_0 \qquad (1)$$

in which:
$E_0$ is the ultrasonographic thickness of said fatty tissue at rest,
$E_P$ is the ultrasonographic thickness of said fatty tissue compressed to the maximum,
5) determination, by calculation, of at least one of the parameters of a hypotonic solution to be administered, said parameter being chosen from the volume and the osmolarity.

For the purpose of the present invention, the ultrasonographic thickness at rest corresponds to the thickness of the hypodermis from the surface of the skin to the muscle membrane (thickness at rest). The ultrasonographic thickness of the tissue compressed to the maximum corresponds to the thickness of the hypodermis from the surface of the skin to the muscle membrane, measured under pressure, for example by pushing on the skin with an ultrasound probe. Specifically, the decrease in the thickness of the subcutaneous tissue is firstly proportional to the pressure exerted, and then, when this pressure reaches a high value, the thickness of the compressed tissue remains constant regardless of the subsequent increase in the pressure. For the purpose of the invention, a sufficient pressure is consequently applied until a constant compressed-tissue thickness value is obtained.

According to one advantageous embodiment of the invention, the calculation of the BI index is carried out by means of software which determines, according to the ultrasonographic data measured in steps 2) and 3), at least one of the following parameters:
the mode of injection of the hypotonic solution, i.e. the injection angle (angle formed by the needle and the surface of the skin) and the space between two injection points;
the osmolarity of the hypotonic solution to be administered;
the volume of the hypotonic solution to be injected point by point.

According to one preferred embodiment of the invention, the volume of hypotonic solution to be injected is equal or portional to the volume of tissue of the area to be treated.

For this, the method also comprises an additional step during which the software calculates the osmolarity of the initial interstitial sector of the patient based on the results of an ionogram. This examination consists in determining the plasma concentrations of sodium, potassium, calcium, magnesium, chlorine and bicarbonate ions, and also the plasma concentrations of proteins and of sugar (glycemia). The Gibbs-Donnan effect (also known as the Donnan effect, Donnan law or alternatively Gibbs-Donnan equilibrium) relates to the biological laws applicable to two compartments separated by a semipermeable membrane and in which one of the compartments contains nondiffusible ions. This model is applied to the vascular and interstitial sector. The vascular sector contains the nondiffusible anions and proteins. The Gibbs-Donnan laws of electroneutrality of each compartment make it possible to calculate the number of anionic and cationic milliequivalents by calculating the plasma anion gap (expressed in mmol/l) represented by the organic acids.

Anions—Cations in milliequivalent.

The proportion of sulfates and phosphates has been considered to be constant and to correspond to the data of the Hanon table (A. Blacque Belair et al., Dictionnaire des Constantes Biologiques et Physiques en Médecine, Applications cliniques pratiques [Dictionary of biological and physical constants in medicine, practical clinical applications], 6th edition, publisher Maloine, 1991) in order to be able to deduce therefrom the plasma osmolarity.

The initial osmolarity of the interstitial sector is equal to the intracellular osmolarity.

The initial osmolarity of the interstitial sector (B) can be calculated by applying the second law according to Gibbs-Donnan concerning the equality of the products of the osmolarities of the diffusible anions by the osmolarity of the diffusible cations between the vascular and interstitial compartments.

These calculations make it possible to determine the level of sodium in the interstitial sector, which is always significantly lower than the plasma sodium level.

The total tissue volume to be treated by injection, the volume of solution to be injected and the osmolarity of the solution to be injected in order to cause the partial effectiveness osmolar gradient should then subsequently be evaluated.

During the evaluation of the volume of the interstitial sector, the amount of sodium initially present should also be calculated: i.e. the product of the initial osmolarity with respect to sodium (J) multiplied by the volume of the interstitial sector (A) and divided by one thousand:

$$\text{Amount of sodium} = A \times J / 1000.$$

Similarly, the amount of initial solute in milliosmole (C) is given by the following formula (2):

$$C = A \times B / 1000 \qquad (2)$$

in which A is the volume of the initial interstitial sector (expressed in milliliters) and B is the initial osmolarity of the interstitial sector (expressed in milliosmoles/liter).

Similarly, the amount of solute injected (F), expressed in milliosmoles, is given by the following formula (3):

$$F = D \times E / 1000 \qquad (3)$$

in which D corresponds to the volume of hypotonic solution to be injected (expressed in milliliters) and E corresponds to the osmolarity of the hypotonic solution to be injected (expressed in milliosmoles per liter).

Once the volume of hypotonic to be injected (D) is determined, it is possible to calculate the osmolarity of the hypotonic solution to be injected (E) in order to create a final or resulting interstitial hypo-osmolarity (H) resulting in the partial effectiveness osmolar gradient (O.G.) according to the following formula (4) such that:

$$\text{Partial effectiveness O.G.} = B - H \qquad (4)$$

The final sodium osmolarity (K) is equal to the sum of the initial amount of sodium present in the interstitial sector and of the amount of sodium injected, the whole being divided by the final volume A+D and then multiplied by one thousand.

It is possible to define a safety index taking into account only the percentage decrease in interstitial sodium osmolarity. This is equal to (J−K)/J.

This index takes the same values as those recognized in vitro, i.e.:

9 g/l−3 g/l/9 g/l=66% for a total effectiveness leading to necrosis of the entire tissue.

According to the invention, the safety index for the esthetic treatment of the fatty and cellulite lumps will therefore preferably remain less than 55%, keeping a safety margin of 10%.

The final interstitial hypo-osmolarity to be achieved in the interstitial sector (H) therefore corresponds to the difference between the initial osmolarity of the interstitial sector (B) and the osmolar gradient to be applied. This osmolar gradient is expressed in milliosmoles per liter and, in the case of the treatment of cellulite, it will correspond to the values of the partial effectiveness osmolar gradient previously defined.

The software uses the initial volume of the interstitial sector (A) expressed in milliliters, the initial osmolarity of the interstitial sector (B) expressed in milliosmoles per liter and the final interstitial hypo-osmolarity to be achieved (H) in milliosmoles per liter.

It is then possible to define:
either the volume of hypotonic solution to be injected (D),
or the osmolarity of the hypotonic solution to be injected (E).

The intermediate calculations reveal the values below:
The amount of initial solute in milliosmoles (C) present in (A), i.e.: C=A×B/1000.

The amount of solute to be injected in milliosmoles (F) present in (D), i.e.: F=D×E/1000.

The final volume (G) expressed in milliliters, which is equal to A+D.

The total amount of solute (I) expressed in milliosmoles, which is equal to C+F.

Thus, on the basis of the general equality of the following formula (5):

$$((A \times B)+(D \times E))/A+D=H \quad (5)$$

it becomes possible to choose:
either D corresponding to the volume of hypotonic solution to be injected,
or E corresponding to the osmolarity of the hypotonic solution to be injected.

According to one preferred embodiment of the invention, D is chosen as being equal to the total tissue volume so as to consider the injection as having an instantaneous diffusion in A. This volume corresponds to a cylinder having a length equal to that of the injection needle and a radius referred to as diffusion radius. Since the injections are spaced out evenly and in parallel, there is a relationship between the space, the needle length, the thickness of the hypodermis at rest, the injection angle and the diffusion radius allowing the cylinders to be contiguous.

This relationship can be expressed by the following formulae (6) and (7):

$$\text{Sine of the injection angle}=E_0/\text{Length of the injection needle} \quad (6)$$

$$\text{Sine of the injection angle}=2\times\text{Diffusion radius/Space between two injection points} \quad (7)$$

As was previously seen, the volume of the initial interstitial sector A is calculated by the software on the basis of the ultrasonographic data by applying formula (1) described above (Bernstein Index).

According to one preferred embodiment of the invention, the destruction of the fatty tissue is promoted through the action of ultrasound on the tissue already made fragile after administration of said hypotonic solution. The lysis of the hyperhydrated adipocytes by causing destruction of the cell membranes is thus more readily obtained.

In this embodiment, the method in accordance with the invention then also comprises a step of applying ultrasound.

In this case, low-frequency ultrasound is preferably used. The destructive effects of said low-frequency ultrasound have been attributed to a mechanism of contact cavitation or to a simple acoustic tension on membranes rendered fragile.

The ultrasonic radiation power that can be received by the skin is limited, owing to skin tolerance, to on average 3 watts per $cm^2$ of skin.

However, according to the esthetic treatment method in accordance with the invention, the application of higher powers over more restricted time ranges is preferably implemented, in order to achieve higher and more effective instantaneous powers. By way of example, an emission time of 0.2 second followed by 0.2 second of silence allows the application of ultrasonic waves with a power of 6 watts/$cm^2$ while respecting the average 3 watts per $cm^2$ tolerated.

In this way, the powers used can reach up to 24 watts/$cm^2$.

According to another preferential embodiment, the method in accordance with the invention also comprises a step of applying vibrations on the predetermined area. This step is carried out on tissues infiltrated after the injections of hypotonic solution (draining vibrations).

This is because the first lipotomies gave rise to unwanted effects such as skin hemosiderosis, the presence of residual fat nodules or a collection of triglycerides. These are eliminated or greatly reduced by the application of vertical draining vibrations allowing part of the injected solution mingled with debris to leave.

According to one preferred embodiment of the method in accordance with the present invention, the vibrations are applied perpendicular to the plane formed by the skin surface.

Mechanical vibrations are readily transmitted deeply and thus allow optimum drainage of the infiltrated area.

These vibrations are obtained by percussion of the skin surface.

The power of the apparatus is advantageously between 112 and 450 watts, preferably 225 watts.

A vibration frequency of around 12 000 oscillations or cycles comprising a to-and-fro movement per minute with a vibratory movement amplitude of between 0.5 and 2 mm were found to be the most effective in causing a considerable exiting flow of the hypotonic solution administered.

Such mechanical vibrations are also subsequently useful in order to prevent the appearance of fibrous nodules.

The method for esthetically treating cellulite skin in accordance with the invention makes it possible to increase the security of the lipotomy technique to a maximum with respect to the risks of overdose, and provides real progress with regard to good reproducibility of the results obtained according to patients and the anatomical areas treated.

Another subject of the invention is therefore a device for esthetically treating cellulite skin by cutaneous injection of at least one hypotonic solution in a predetermined area of fatty tissue to be treated (lipotomy), characterized in that it comprises:
at least one ultrasound-generating apparatus, at least one ultrasound probe capable of measuring the thickness of said fatty tissue at rest and at maximum compression in said area, at least one data processing software, in particular capable of calculating the percentage (BI or Bernstein Index) represented by the volume of the extracellular sector of said tissue in said area according to the following equation (1):

$$BI\,(\%) = E_0 - E_P/E_0 \qquad (1)$$

in which:
- $E_0$ is the ultrasonographic thickness of said fatty tissue at rest,
- $E_P$ is the ultrasonographic thickness of said fatty tissue compressed to the maximum, and at least one skin injector capable of delivering injections of at least one hypotonic solution which are oblique and/or perpendicular to the skin surface.

According to one preferred embodiment of the invention, said device also comprises at least one apparatus generating vibrations perpendicular to the skin surface of said fatty tissue (called vibro-drainer).

The vibrations applied by this device preferably have a frequency of around 12 000 oscillations or cycles per minute.

Advantageously, the software integrated into this device also calculates, on the basis of the ultrasonographic data, at least one of the following parameters:
- the mode of injection of the hypotonic solution, i.e. the injection angle and the space between two injection points,
- the osmolarity of the hypotonic solution to be administered,
- the volume of the hypotonic solution to be injected point by point.

According to one preferred embodiment of the invention, the device also comprises a computer system for controlling and automatically delivering injections of the hypotonic solution, the volume of which is directly deduced from the ultrasonographic measurements.

Finally, according to one preferred embodiment of this device, the ultrasound is low-frequency ultrasound and the working mode thereof makes it possible to deliver instantaneous powers of 3 to 24 watts/square cm while respecting an average power of 3 watts per square centimeter by virtue of a sequential emission.

By way of example, the clinical study below illustrates the disclosure of the invention.

Figure 2:
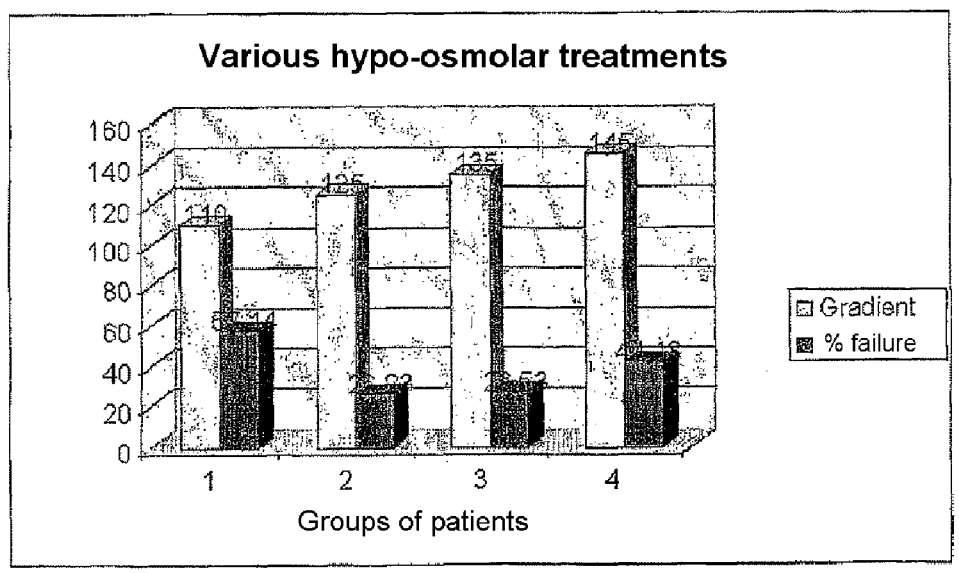
Figure 3:
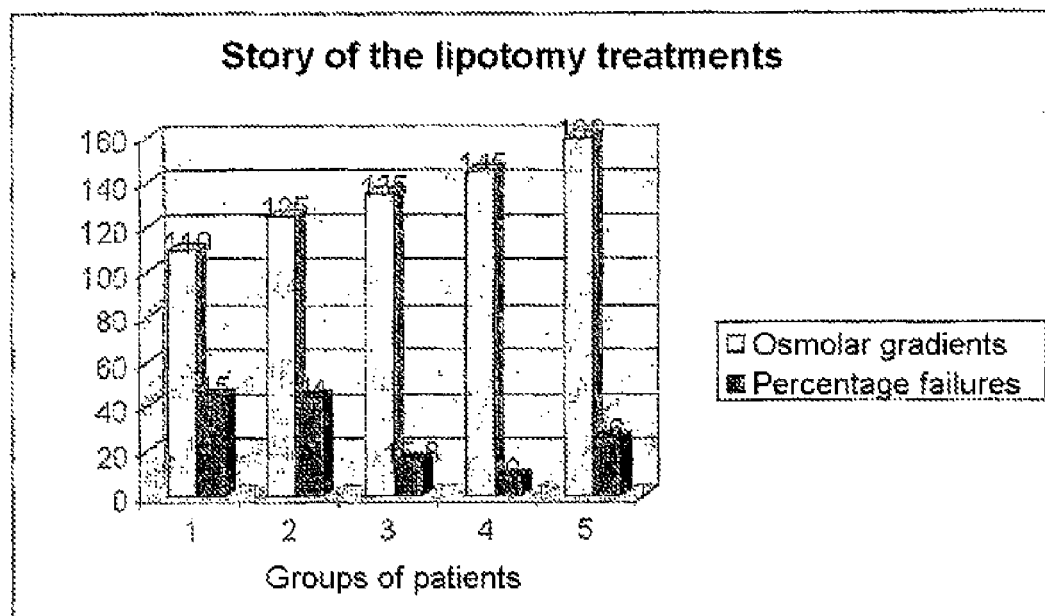

In addition to the above arrangements, the invention also comprises other arrangements which will emerge from the following description, which refers to a comparative clinical study according to a conventional lipotomy method which is not part of the invention, to an example of demonstration of the importance of the injection angle in a lipotomy method, and to the appended FIGS. 1 to 3 in which:

FIG. 1 represents a sectional scheme of an area of fatty tissue to be treated, on which the hypodermal thickness, the space between two injection points, the length of the injection needle, double the diffusion radius and the injection angle can be observed, FIGS. 2 and 3 are graphs giving the effectiveness results of a comparative study of effectiveness of treatments of fatty tissues by lipotomy according to methods not in accordance with the invention. On these graphs, the effectiveness and the absence of effectiveness depend on the osmolar gradients used.

EXAMPLE 1

Comparative Clinical Study According to a First Conventional Lipotomy Method which is not Part of the Invention A clinical study implementing a conventional lipotomy method which is not part of the present invention was carried out on a panel of 394 individuals in order to create an element of comparison of the effectiveness of the method in accordance with the invention.

1) Inclusions and Contraindications

The individuals included in this study all had one or more localized fatty or cellulite lumps.

Individuals suffering from liver or renal failure, from angina, from a coagulation disorder or from an immune disorder were excluded from the study.

As a precaution, pregnant women and applications which appeared to be the result of a psychic disorder were also excluded from the study.

Ionograms were not carried out on all the individuals accepted into the study and a possible variation in plasma sodium level between 142 and 135 milliosmol/liter had to be taken into account, this being reflected by uncertainty regarding the gradient of 13 milliosmol/liter and regarding the interstitial sodium hypo-osmolarity index of 5%.

The results will therefore be analyzed while respecting the error range:
=either −13 milliosmol/liter of gradient
=or +5% of sodium hypo-osmolarity coefficient.

2) Materials

The following materials were used to implement the method in accordance with the invention:
- syringes and needles (0.3/13, 0.8/5, 1.2/5),
- three-way valve and tubes,
- small rulers,
- water for injectable preparation,
- lidocaine, adrenalin, sodium chloride at 10%,
- physiological saline,
- ultrasound apparatus, frequency 25 kHz, power 3 W/cm², sold by the company Biophoton under the reference USL 2H $CE_{0459}$,
- vibro-draining apparatus sold by the company Biophoton under the reference VBS 10-200 $CE_{0459}$,
- sterile ultrasound gel,
- software: the ionogram and the ultrasonographic measurements are captured so as to obtain, according to the gradient chosen: the volume of solution per injection, the dilution, the space between each injection and the injection angle,
- sterile gloves,
- sterile drapes.

3) Method

Each individual was photographed from the front or from the side and the circumference of the area to be treated was measured. The areas were then drawn in pencil, revealing a major axis and a width. The injection points were spaced every centimeter widthwise and according to a variable measurement between 1 cm and 5 cm lengthwise according to the fatty tissue thickness.

The fatty tissue thickness was then measured using an ultrasound probe, at the level of the maximum thickness and of the minimum thickness of the area to be treated, at rest and in the compressed position.

The ultrasonographic measurements and the biological analysis results were captured by processing software.

394 areas were thus treated.

The osmolarity gradients applied varied from 99 milliosmol per liter to 170 milliosmol, and the interstitial sodium osmolarity coefficient was calculated, taking care to ensure that it always remained less than or equal to 55%.

In this study, it changed between 36% and 55%.

The software indicates, according to the effectiveness gradient retained, the dilution and the volume per injection. In this study, which is presented by way of comparison and which is not therefore part of the invention, the space between each injection and the angle of introduction of the needle were not determined by the software.

The areas to be treated were disinfected according to a four-step protocol: washing comprising betadine, rinsing, drying, and then disinfection with dermal betadine.

Before their use, the small rulers and the ultrasonic heads were sterilized by soaking in a cold-sterilization bath.

The treatment bottles were attached to a bracket, while the injection material rested on a sterile drape.

The vibro-draining apparatus was placed in a sterile cover.

On each individual, the first injections were carried out in a dermal-epidermal manner in order to anesthetize each point, using the 0.3/13 needles and the hypotonic treatment solution cooled to 5° C.

The hypotonic solution was then injected with 0.8/50 needles, adhering to the information from the software and filling the syringe with the tree-way valve.

Less than 30 minutes later, the external ultrasound was applied for a period of approximately 5 minutes.

A second series of injections was carried out with the 1.2/50 needles, using a physiological saline.

Finally, the draining vibration phase was carried out in order to externalize a part of the injected solution.

Sterile compresses were placed so as to cover the area treated, which would continue to ooze for 24 hours.

A support garment was worn by each individual for one month, during the daytime only.

One month later, each individual returned in order to undergo a treatment of draining injections consisting of injections of physiological saline and vibrations.

The results were evaluated four months later, on the basis of the patient's assessment, the photographs and the measurements of circumference of the area treated.

In order to be able to compare the results, analytical software was designed so as to indicate the osmolarity gradient, the interstitial sodium osmolarity safety index and also the percentage represented by the diffusion volume compared with the treated volume.

4) Results:

The results classified only according to the recalculated gradients are reported in the appended FIG. 2. This graph represents the effectiveness or ineffectiveness of the method according to the osmolar gradients applied.

These results show an ineffectiveness for osmolar gradients of less than 125 milliosmol/liter and a lesser result when the gradient exceeds 145 milliosmol/liter.

These results show a considerable failure rate, which is explained by the absence of geometric parameter setting during the oblique injections and the consequence thereof on the error in evaluating the tissue volume really treated.

This type of result corresponds to most of the hypo-osmolar lysis treatments currently in vogue. Said treatments, moreover, combine several nonsynergistic techniques in order to make up for their lack of effectiveness, therefore making any analysis impossible.

EXAMPLE 2

Demonstration of the Importance of the Angle of Injection

1) Analysis

The results of the study presented above in example 1 were reproduced while eliminating all the oblique injections carried out without the angle of injection being indicated, and retaining only the injections perpendicular to the skin surface. The results obtained are represented in the appended FIG. 3, on which the effectiveness or ineffectiveness of the method is given according to the various osmolar gradients used.

In this figure, the following are noted:

osmolar gradient from 100 to 120 milliosmol/liter: 45% failure osmolar gradient from 120 to 130 milliosmol/liter: 44% failure osmolar gradient from 130 to 140 milliosmol/liter: 15.8% failure osmolar gradient from 140 to 150 milliosmol/liter: 9% failure osmolar gradient greater than 150 milliosmol/liter: 26% failure.

It is noted here that the failure rate is less than that obtained in example 1 above, which is explained by the diffusion of the solution in 100% of the tissue treated. A curve resembling that of the previous FIG. 2 is noted, with failure rates increased when the osmolar gradient is either less than 135 milliosmol/liter, or greater than 160 milliosmol/liter.

The loss of effectiveness observed for osmolar gradients of greater than 160 milliosmol/liter can be interpreted as being the consequence of a ceiling reached in the increase in cell volume. This is because this increase in volume is accompanied by dilation of the membrane pores and a maximum porosity of the membrane. Starting from 150 milliosmol/liter of gradient, the osmosis effect no longer increases and only the inflammatory phenomena are accentuated.

Under these circumstances, a treatment which risks being dangerous and ineffective is obtained.

Comparison of the two FIGS. 2 and 3 therefore justifies the approach of improving the lipotomy method which is the subject of the present invention by emphasizing the geometric rules for injection in such a way that the oblique angles of injection make it possible to involve 100% of the tissue volume treated according to the rule already stated above:

$$\text{Sin(injection angle)} = \frac{\text{Hypodermal thickness}}{\text{Needle length}} = \frac{\text{Double diffusion radius}}{\text{Space}}$$

Furthermore, the osmolar gradient effectiveness range is relatively small, approximately 10 milliosmol/liter, which gives importance to the ionogram evaluating the initial interstitial osmolarity since said osmolarity is capable of causing the gradient to vary by 13 milliosmol/liter, as was seen above in example 1.

In conclusion, the method in accordance with the invention makes it possible to improve the current lipotomy method, in particular its reproducibility and its working safety, provided that rigorous parameter setting is adhered to.

Under these conditions, lipotomy represents a good alternative to liposuction.

The invention claimed is:

1. A method for esthetically treating cellulite skin of a patient by lipotomy, characterized in that it comprises at least the following steps:
   1) determination of the skin surface of an area to be treated by means in particular of a grid on the skin,
   2) ultrasonographic evaluation of the volume of fatty tissue underlying said surface of the area to be treated, at rest,
   3) ultrasonographic evaluation of the volume of fatty tissue underlying said surface of the area to be treated, said tissue being compressed to the maximum,
   4) calculation of the percentage (BI or Bernstein Index) represented by the volume of the extracellular sector of said tissue in said area, considering the volume represented by the cells of the fatty tissue to be incompressible, according to the following equation (1):

$$BI\,(\%) = E_0 - E_P / E_0 \qquad (1)$$

in which:
   $E_0$ is the ultrasonographic thickness of said fatty tissue at rest,
   $E_P$ is the ultrasonographic thickness of said fatty tissue compressed to the maximum,
   5) determination, by calculation, of at least one of the parameters of a hypotonic solution to be administered, said parameter being chosen from the volume and the osmolarity.

2. The method as claimed in claim 1, characterized in that the calculation of the BI index is carried out by means of software which determines, according to the ultrasonographic data measured in steps 2) and 3), at least one of the following parameters:
   the mode of injection of the hypotonic solution,
   the osmolarity of the hypotonic solution to be administered;
   the volume of the hypotonic solution to be injected point by point.

3. The method as claimed in claim 1 or 2, characterized in that the volume of hypotonic solution to be injected is equal or proportional to the volume of tissue of the area to be treated.

4. The method as claimed in claim 3, characterized in that it also comprises an additional step during which the software calculates the osmolarity of the initial interstitial sector of the patient on the basis of the results of an ionogram.

5. The method as claimed in claim 1 or 2, characterized in that it also comprises a step of applying ultrasound.

6. The method as claimed in claim 1 or 2, characterized in that it also comprises a step of applying vibrations on the predetermined area.

7. The method as claimed in claim 6, characterized in that the vibrations are applied perpendicular to the plane formed by the skin surface.

8. A device for esthetically treating cellulite skin by cutaneous injection of at least one hypotonic solution in a predetermined area of fatty tissue to be treated (lipotomy), characterized in that it comprises:
   at least one ultrasound-generating apparatus,
   at least one ultrasound probe capable of measuring the thickness of said fatty tissue at rest and at maximum compression in said area,
   at least one data processing software, in particular capable of calculating the percentage (BI or Bernstein Index) represented by the volume of the extracellular sector of said tissue in said area according to the following equation (1):

$$BI\,(\%) = E_0 - E_P / E_0 \qquad (1)$$

in which:
   $E_0$ is the ultrasonographic thickness of said fatty tissue at rest,
   $E_P$ is the ultrasonographic thickness of said fatty tissue compressed to the maximum, and
   at least one skin injector capable of delivering injections of at least one hypotonic solution which are oblique and/or perpendicular to the skin surface.

9. The device as claimed in claim 8, characterized in that it also comprises at least one apparatus generating vibrations perpendicular to the skin surface of said fatty tissue.

10. The device as claimed in claim 9, characterized in that the vibrations have a frequency of around 12 000 oscillations or cycles per minute.

11. The device as claimed in any one of claims 8 to 10, characterized in that the software also calculates, on the basis of the ultrasonographic data, at least one of the following parameters:
    the mode of injection of the hypotonic solution,
    the osmolarity of the hypotonic solution to be administered,
    the volume of the hypotonic solution to be injected point by point.

12. The device as claimed in any one of claims 8 to 10, characterized in that it also comprises a computer system for controlling and delivering, automatically, injections of the hypotonic solution of which the volume is directly deduced from the ultrasonographic measurements.

13. The device as claimed in any one of claims 8 to 10, characterized in that the ultrasound is low-frequency ultrasound and the working mode thereof makes it possible to deliver instantaneous powers of 3 to 24 watts/square centimeter while at the same time respecting an average power of 3 watts per square centimeter by virtue of a sequential emission.

* * * * *